United States Patent
Saito et al.

(10) Patent No.: US 9,874,517 B2
(45) Date of Patent: Jan. 23, 2018

(54) PROCESSING APPARATUS AND PARTICLE SECURING METHOD

(71) Applicant: Konica Minolta, Inc., Chiyoda-ku, Tokyo (JP)

(72) Inventors: Keita Saito, Toyokawa (JP); Midori Shimomura, Hino (JP); Dai Suwama, Hachioji (JP); Sayaka Morita, Gamagori (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 205 days.

(21) Appl. No.: 14/644,717

(22) Filed: Mar. 11, 2015

(65) Prior Publication Data

US 2015/0268165 A1 Sep. 24, 2015

(30) Foreign Application Priority Data

Mar. 24, 2014 (JP) ................................ 2014-060866

(51) Int. Cl.
*G01N 21/00* (2006.01)
*G01N 21/49* (2006.01)
*G01N 21/55* (2014.01)

(52) U.S. Cl.
CPC ............ *G01N 21/49* (2013.01); *G01N 21/55* (2013.01); *G01N 2201/06146* (2013.01); *G01N 2201/124* (2013.01)

(58) Field of Classification Search
CPC ........ G01N 21/49; G01N 21/55; H01L 21/00; H01L 23/58; C23C 16/52; B05C 11/10
See application file for complete search history.

(56) References Cited

U.S. PATENT DOCUMENTS

2006/0228897 A1* 10/2006 Timans ............ H01L 21/67115
  438/758
2010/0086670 A1* 4/2010 Kushibiki ............... C23C 16/52
  427/8

FOREIGN PATENT DOCUMENTS

| JP | 63-073628 A | 4/1988 |
| JP | 2002-39723 A | 2/2002 |
| JP | 2002-273308 A | 9/2002 |

(Continued)

OTHER PUBLICATIONS

Office Action (Notice of Reasons for Rejection) dated Mar. 1, 2016, by the Japanese Patent Office in corresponding Japanese Application No. 2014-060866 and English Translation. (6 pages).

(Continued)

*Primary Examiner* — Abdullahi Nur
(74) *Attorney, Agent, or Firm* — Buchanan Ingersoll & Rooney PC

(57) ABSTRACT

A processing apparatus includes: a light emission unit configured to emit light to a surface of a particle dispersed liquid applied to a base material, the particle dispersed liquid having particles dispersed in a solvent; a reflected light amount monitoring unit configured to detect an amount of the light reflected, and monitor a temporal variation of the detected value; and a condition adjustment unit configured to adjust a condition for a particle securing process, the particle securing process being performed to remove the solvent and secure the particles onto the base material, wherein, when the temporal variation falls within a predetermined range after the value has reached an extreme value, securing of the particles is determined to have been completed.

11 Claims, 6 Drawing Sheets

(56) References Cited

FOREIGN PATENT DOCUMENTS

| | | |
|---|---|---|
| JP | 2007-179819 A | 7/2007 |
| JP | 2008-225093 A | 9/2008 |

OTHER PUBLICATIONS

English Translation of Office Action (Notice of Reasons for Rejection) dated Aug. 4, 2016, by the Japanese Patent Office in corresponding Japanese Patent Application No. 2014-060866. (5 pages).

* cited by examiner

PROCESSING APPARATUS AND PARTICLE SECURING METHOD

The entire disclosure of Japanese Patent Application No. 2014-060866 filed on Mar. 24, 2014 including description, claims, drawings, and abstract are incorporated herein by reference in its entirety.

BACKGROUND OF THE INVENTION

Field of the Invention

The present invention relates to a processing apparatus that performs a process (such as a calcination process) to secure the particles in a particle dispersed liquid onto a base material, and a particle securing method using the processing apparatus.

Description of the Related Art

In manufacturing printed circuit boards, membrane switches, and electrode units of electronic devices and the like, a subtractive process involving etching is conventionally used. However, a subtractive process requires a large number of complicated steps and a lot of equipment. In addition to that, a subtractive process has low efficiency in the use of material, resulting in high production costs.

As a manufacturing method that can solve these problems with a subtractive process, so-called printed electronics (PE) is drawing attention these days. In PE, a particle dispersed liquid in which metal nanoparticles or the like having electrical functions are dispersed is applied onto a base material by a printing technique. In PE, the particle dispersed liquid applied onto the base material is calcined, so that the particles are secured onto the base material.

Specifically, after the particle dispersed liquid is applied onto the base material, the solvent and the dispersant are removed from the particle dispersed liquid by action of heat, light, chemical energy, or the like. As a result, the particles are bonded to one another, and are secured as a film having the function of the particles onto the base material. If the amount of calcination energy supply is too small when such a calcination process is performed, the solvent, the dispersant, or non-bonded particles remain, and the function of the formed film cannot be sufficiently achieved, resulting in defective conduction or the like. If an excessive amount of calcination energy is supplied, on the other hand, the base material might be damaged.

So as to avoid such problems, a method of controlling calcination conditions through a comparison with the absolute value of an already measured amount of light reflected from a test pattern has been suggested (see JP 2008-225093 A, for example).

According to the technique disclosed in JP 2008-225093 A, however, variations appear in the molten state and the bonding state of the particles due to variations in respective conditions, and, in some cases, it is difficult to perform calcination by the right amount. The respective conditions may include the attachment position of the detector, the attachment position of the light source, temporal or spacial fluctuations in the amount of light emitted from the light source, the pattern to be formed, the type and the thickness of the base material, the amount of discharged ink, the type and the amount of ink, environmental conditions, and the like.

JP 63-73628 A discloses a technique of determining the state of a liquid based on a relative value of a detection signal, not on the absolute value of the detection signal. However, by the technique disclosed in JP 63-73628 A, only the existence of a liquid is detected, and particle binding and other phenomena cannot be detected.

SUMMARY OF THE INVENTION

In view of the above problems, an object of the present invention is to provide a processing apparatus that can perform a process such as calcination in a more appropriate manner regardless of variations in respective conditions, and a particle securing method using the processing apparatus.

To achieve the abovementioned object, according to an aspect, a processing apparatus that performs a particle securing process on a particle dispersed liquid applied to a base material to remove a solvent and secure particles onto the base material, reflecting one aspect of the present invention, comprises: a light emission unit that emits light to the surface of the particle dispersed liquid; a reflected light amount monitoring unit that detects the amount of the light reflected, and monitors a temporal variation of the detected value; and a condition adjustment unit that adjusts conditions for the particle securing process, wherein, when the temporal variation falls within a predetermined range after the value has reached the extreme value, the securing of the particles is determined to have been completed.

With this structure, a process such as calcination can be performed in a more appropriate manner, regardless of variations in respective conditions.

In the above structure, the particle securing process is preferably a process of calcining the particle dispersed liquid through a supply of calcination energy, and, when the securing of the particles by calcination is determined to have been completed, the supply of calcination energy is preferably suspended.

In the above structure, the reflected light amount monitoring unit preferably calculates the temporal variation by recognizing the value in each predetermined time interval, and calculating the difference between the value and the value detected last time. Further, the predetermined range is preferably set as a range within ±2% of the detected amount of the light reflected.

In the above structure, a plurality of pairs of light emission units and reflected light amount monitoring units are preferably installed to detect amounts of reflected light at different locations on the surface, the light emission unit corresponding to the reflected light amount monitoring unit with each other. With this structure, the determination can be performed in a more appropriate manner.

To achieve the abovementioned object, according to an aspect, a particle securing method using the processing apparatus having the above structure to secure the particles onto the base material, reflecting one aspect of the present invention, comprises: a first step of coating a surface of the base material with an antireflection film, the particle dispersed liquid being applied to the surface of the base material; a second step of applying the particle dispersed liquid to the base material after the first step is carried out; and a third step of causing the processing apparatus to perform the particle securing process after the second step is carried out. By this method, a decrease in the accuracy of the determination due to influence of the amount of light reflected from a portion of the base material can be prevented as much as possible.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of the present invention will be described with an example of a calcination apparatus with reference to the drawings. However, the scope of the invention is not limited to this embodiment.

Figure 1:
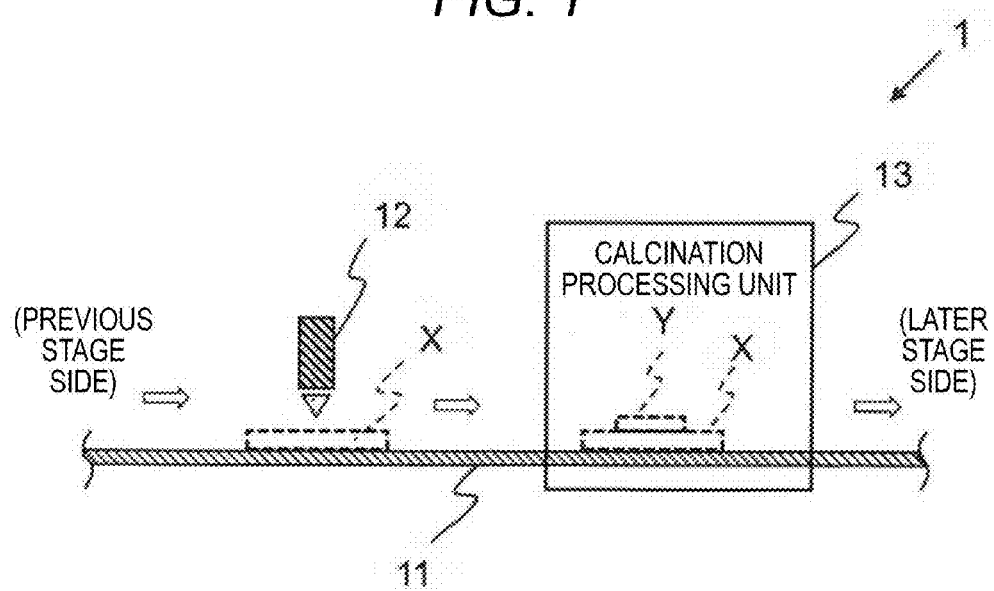
FIG. 1 is a diagram schematically showing the structure of a calcination apparatus according to this embodiment.

FIG. 1 is a diagram schematically showing the structure of a calcination apparatus 1 according to this embodiment. As shown in this drawing, the calcination apparatus 1 includes a conveyance unit 11, an application unit 12, and a calcination processing unit 13. The calcination apparatus 1 applies a particle dispersed liquid Y to a base material X, and performs calcination (an example of a process of removing the solvent of the particle dispersed liquid Y and securing the particles onto the base material X) on the particle dispersed liquid Y, to form a wiring pattern on the base material X.

As for the base material X, a type and a size suitable for the purpose of use can be selected. As for the type, a resin material such as PET is used to ensure transparency, an elastic material such as a silicone rubber sheet is used to achieve stretching properties, and a glass material or the like can be used to achieve heat resistance. As for the size, a base material of a necessary size may be used when single base material is only required for one article, or may be divided into base materials of a necessary size in a later stage. Other than the above, the base material X can be in various forms.

As for the particle dispersed liquid Y, a type suitable for the purpose of use can be selected. In a case where a conductive pattern is produced, for example, a metal ink in which metal particles as a conductive material are dispersed can be used. The type of the metal here may be Ag or Cu, for example. A non-metal conductive material may be metal nanowire, CNT, or a conductive polymeric material, for example, and particles of one of these materials may be used.

The size of the particles dispersed in the particle dispersed liquid Y is preferably several hundreds of micrometers to several nanometers. Particularly, a size between several tens of nanometers and several nanometers is preferable, so as to facilitate binding of the particles and handling of the particles. The dispersant and the solvent of the particle dispersed liquid Y can be appropriately changed in accordance with the type of the above described conductive material or the form of application unit 12 or the like. In the description below, metal nanoparticles are dispersed in the particle dispersed liquid Y, for example.

The conveyance unit 11 conveys the base material X set beforehand on the calcination apparatus 1 from the previous stage side (the left side in FIG. 1) to the later stage side (the right side in FIG. 1). More specifically, the conveyance unit 11 performs the process of conveying the base material X from the previous stage side to the position corresponding to the application unit 12, the process of conveying the base material X having the particle dispersed liquid Y applied thereto by the application unit 12 to the calcination processing unit 13, and the process of conveying the base material X subjected to a calcination process further to the later stage side.

The conveyance unit 11 may be a transfer roller that is rotated while having the base material X placed on the outer peripheral surface thereof. In this case, the transfer roller is rotationally attached with the drive motor, for example, and is designed to rotationally convey the base material X secured onto the outer peripheral surface with an adhesive agent or by suction. The base material X may be set in an appropriate position by a manual operation, instead of the conveyance unit 11.

The application unit 12 applies the particle dispersed liquid Y to the site where the wiring pattern is to be formed on the surface of the base material X. The application method used by the application unit 12 may be an ink jet method, a wet electrophotographic method, a plateless printing method using a dispenser, or a plate printing method such as screen printing, gravure printing, or flexographic printing, for example.

However, there is normally a need to select a purpose of use and a particle dispersed liquid Y that are suitable for each of the application methods. In a case where a conductive ink is applied by an ink jet method, for example, the ink needs to be adjusted to a viscosity of 3 to 15 mPa·sec, and a surface tension of approximately 26 to 40 mN/m. As for the use, an ink jet method is not suitable for a wire that is required to be thick, but screen printing may be preferable in that case.

Figure 2:
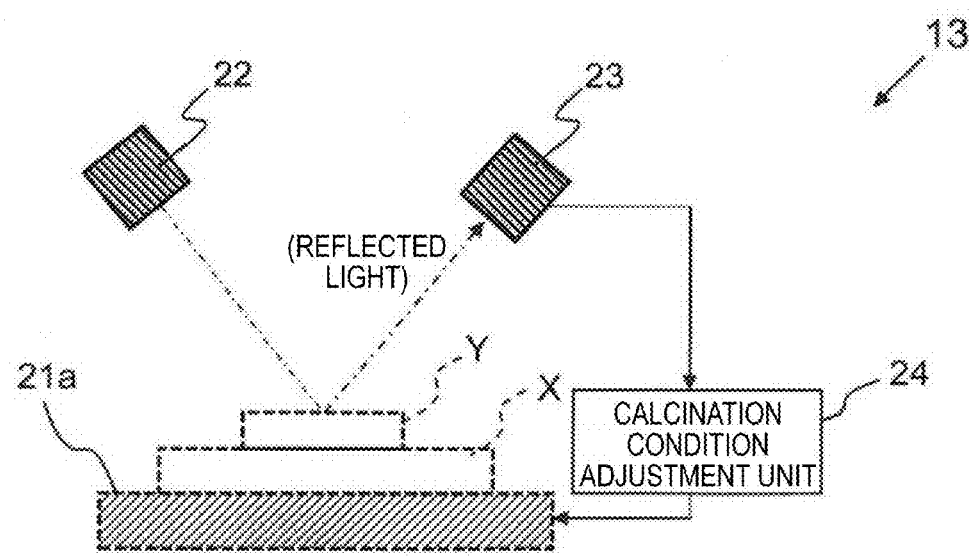
FIG. 2 is a diagram showing a calcination processing unit in greater detail.

The calcination processing unit 13 performs the process of appropriately calcining the particle dispersed liquid Y applied onto the base material X. FIG. 2 is a diagram showing the calcination processing unit 13 in greater detail. As shown in this drawing, the calcination processing unit 13 includes a calcination unit 21a, a light emission unit 22, a reflected light amount monitoring unit 23, and a calcination condition adjustment unit 24.

The calcination unit 21a calcines the particle dispersed liquid Y by removing the solvent and the dispersant of the particle dispersed liquid Y, and supplying energy (calcination energy) for binding particles. The calcination unit 21a of this embodiment supplies heat as the calcination energy, and is in the form of a hot plate that calcines the particle dispersed liquid Y mainly by heat conduction.

The details of the operation (including a stop of the calcination energy supply) of the calcination unit 21a is adjusted by the calcination condition adjustment unit 24.

The specific form of the calcination unit is not limited to the above described form. Some modifications of the calcination unit will be described later.

The light emission unit 22 emits light for sensing the surface state of the particle dispersed liquid Y applied onto the base material X. The light emission unit 22 is placed in such a position that it does not interfere with reflected light and the other components. In a case where the spot to which light is emitted is narrowed, a lens or the like may be used as part of the light source module of the light emission unit 22. So as to prevent such a light source module from interfering with reflected light and the other components, the light emission unit 22 is preferably placed in a position that is located several millimeters to several tens of millimeters away from the surface of the base material X, for example.

Light from the light emission unit 22 may be guided to the surface of the base material X through an optical fiber. The wavelength band of the light emission unit 22 include wavelengths at which particles are reflected or absorbed, or wavelength at which particles are allowed to pass. The wavelength band of the light emission unit 22 is preferably a short-wavelength region of ultraviolet light with substantially the same size as nanoparticles. Accordingly, reflection intensity can be increased through a phenomenon such as Rayleigh scattering or Mie scattering, and measurement sensitivity can be improved.

Light emitted from the light emission unit 22 may be continuous light or pulsed light, but continuous light is preferable in that a temporal variation (temporal changes) of the amount of light is detected as appropriately as possible. The intensity of light emitted from the light emission unit 22 is such an intensity as to ensure the amount of light to allow the reflected light amount monitoring unit 23 to sense reflected light. The type of the light source may be a light bulb, a halogen lamp, a kind of LED, or a laser, for example, but is not limited to them.

The reflected light amount monitoring unit 23 detects the amount of light (reflected light amount) emitted from the light emission unit 22 and reflected by the surface of the particle dispersed liquid Y, and monitors the temporal variation of the detected value. The reflected light amount monitoring unit 23 may be designed to detect the amount of specularly-reflected light, or may be designed to detect the amount of diffusely-reflected light (scattered light).

In a case where the reflected light amount monitoring unit 23 is designed to detect the amount of specularly-reflected light, the reflected light amount monitoring unit 23 is placed in a position at a reflection angle that is equal to the incidence angle. In a case where the reflected light amount monitoring unit 23 is designed to detect the amount of diffusely-reflected light, the reflected light amount monitoring unit 23 is placed in a position at a reflection angle that differs from the incidence angle. The required value of the distance between the base material X or the particle dispersed liquid Y and the reflected light amount monitoring unit 23 varies with the reflected light intensity or the intensity of light emitted from the light emission unit 22, but, in general, the reflected light amount monitoring unit 23 is preferably placed in a position optically conjugate to the light emission unit 22.

The reflected light amount monitoring unit 23 may have a lens in such a position that it can collect reflected light, and reflected light enters the reflected light amount monitoring unit 23. The reflected light that has entered the reflected light amount monitoring unit 23 may be guided to a desired site through an optical fiber. For example, in a case where part of the reflected light amount monitoring unit 23 is placed outside the calcination apparatus 1, reflected light may be guided to the outside position through an optical fiber. The reflected light amount monitoring unit 23 may be designed to detect the amount of reflected light of a specific wavelength through wavelength selection using a color filter or by spectroscopy using a diffraction grating or a prism.

Figure 3:
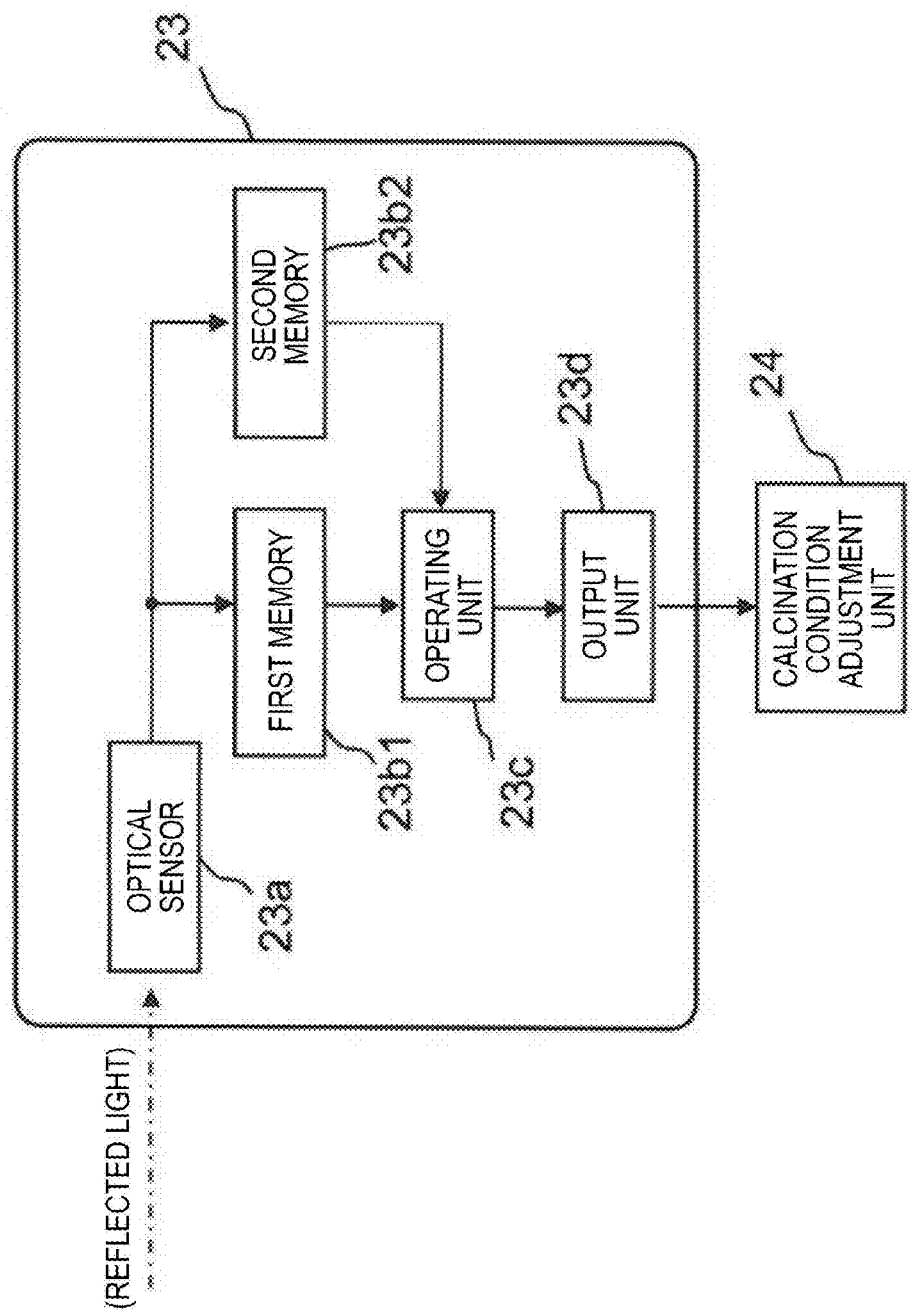
FIG. 3 is a diagram showing, in greater detail, a reflected light amount monitoring unit and the periphery thereof.

FIG. 3 is a diagram showing, in greater detail, the reflected light amount monitoring unit 23 and the periphery thereof. As shown in the drawing, the reflected light amount monitoring unit 23 includes an optical sensor 23a, a first memory 23b1, a second memory 23b2, an operating unit (an operator) 23c, and an output unit 23d.

The optical sensor 23a is a sensor for detecting an amount of reflected light, and various kinds of optical sensors (such as a photodiode, a CCD sensor, a CMOS sensor, or a photoelectron multiplier) can be used. In terms of reflection characteristics of particles and the size of the apparatus, a Si photodiode or the like having its sensitivity peak in a short-wavelength region of ultraviolet light or the like that can readily reflect (scatter) nanoparticles is particularly suitable as the optical sensor 23a. A value detected by the optical sensor 23a is output as the voltage value corresponding to the amount of the reflected light at the time, for example.

A value detected by the optical sensor 23a is recorded into the first memory 23b1 or the second memory 23b2 at predetermined time intervals (at intervals of several seconds, for example). More specifically, respective values successively detected at predetermined intervals are alternately recorded into the first memory 23b1 and the second memory 23b2. That is, the nth, (n+2)th, (n+4)th, . . . detected values are recorded into the first memory 23b1, and the (n+1) th, (n+3)th, (n+5)th, . . . detected values are recorded into the second memory 23b2, with n being an integer. The first memory 23b1 and the second memory 23b2 may be individual memories, or one memory may function as both the first memory 23b1 and the second memory 23b2.

The operating unit 23c calculates a temporal variation of the latest detected value by successively performing a difference calculation (subtraction) using the values recorded in the first memory 23b1 and the second memory 23b2. For example, immediately after the (n+1)th value is recorded into the second memory 23b2, the operating unit 23c calculates a temporal variation of the detected value (the size of the change in one of the above described time intervals) by subtracting the nth value (recorded in the first memory 23b1) from the (n+1)th value (recorded in the second memory 23b2). The result of the calculation is regarded as the temporal variation of the detected value. In this manner, the calcination apparatus 1 recognizes the detected value in each of the above described time intervals, and calculates the temporal variation of the detected value by subtracting the previous value from the detected value.

The output unit 23d outputs an adjustment signal generated based on the result of the operation performed by the operating unit 23c, to the calcination condition adjustment unit 24. The calcination condition adjustment unit 24 adjusts the calcination conditions based on the adjustment signal received from the output unit 23d.

Figure 4:
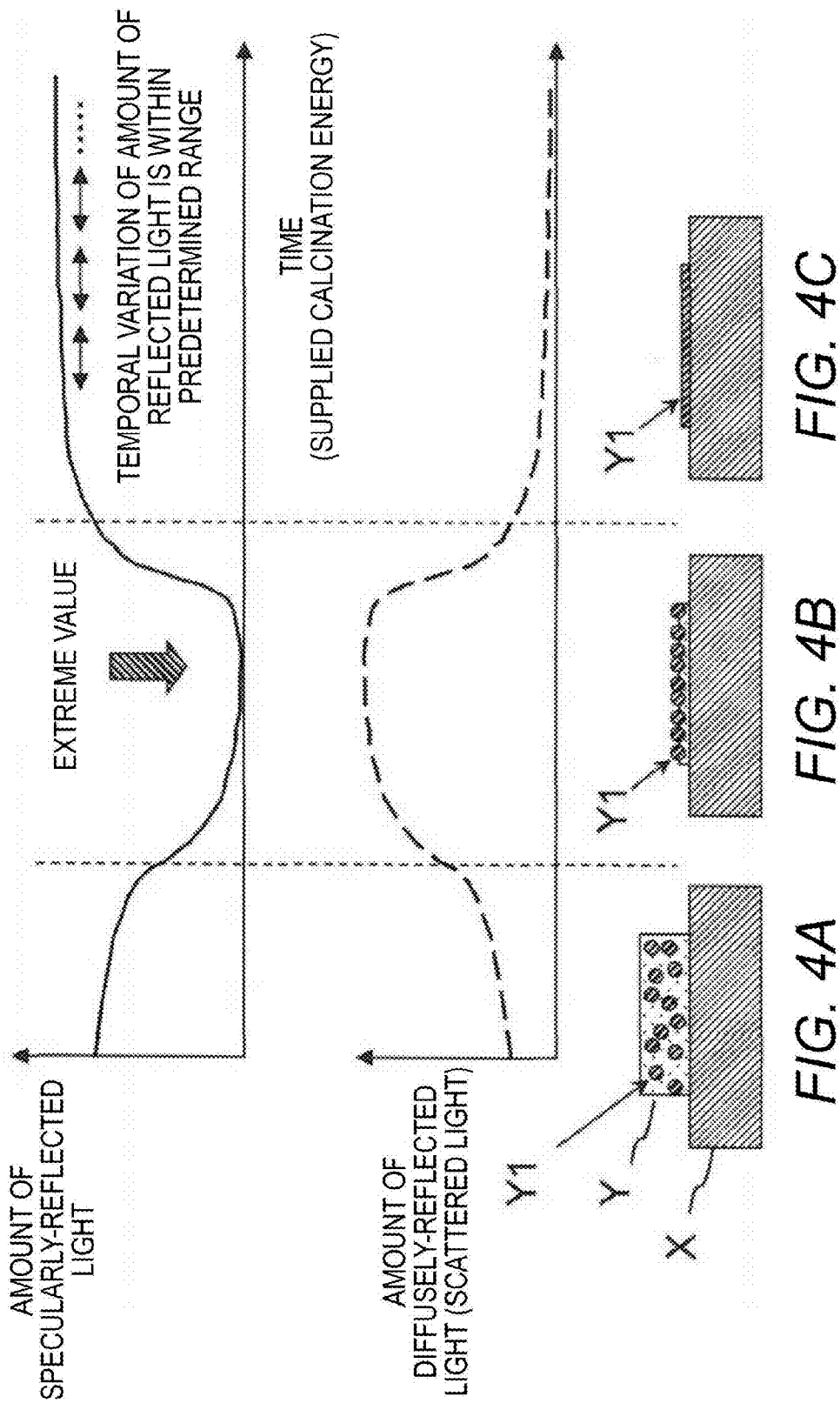
FIG. 4A shows a graph indicating the relationship between amount of reflected light and time during a calculation process.
FIG. 4B shows a graph indicating the relationship between amount of reflected light and time during a calculation process.
FIG. 4C shows a graph indicating the relationship between amount of reflected light and time during a calculation process.

FIG. 4 shows graphs indicating the relationship between an amount of reflected light and time (supplied calcination energy) during a calcination process. The upper graph in FIG. 4 is a graph of the amount of specularly-reflected light, and the lower graph is a graph of the amount of diffusely-reflected light (scattered light amount). In a lower side of FIG. 4, changes caused in the stage of the particle dispersed liquid Y by a supply of calcination energy are schematically shown.

At the start of the supply of calcination energy, the solvent fully exists in the particle dispersed liquid Y, and particles Y1 are dispersed in the solvent, as shown in FIG. 4A. As the calcination energy is supplied in this situation, the solvent and the dispersant are gradually removed from the particle dispersed liquid Y, and the particles Y1 starts being exposed through the surface as shown in FIG. 4B. In this process, diffusely-reflected light gradually increases while specularly-reflected light gradually decreases.

As the supply of the calcination energy is continued further, bonding between the particles becomes obvious, and the surface gradually flattens. In this process, diffusely-reflected light gradually decreases while specularly-reflected light gradually increases. After the bonding between the particles is completed as shown in FIG. 4C, or after the calcination is completed, the shape of the surface hardly changes. Therefore, there is hardly a temporal variation in the amount of reflected light, and the amount of reflected light is substantially constant.

Since the surface of the particle dispersed liquid Y changes in the above described manner, the amount of specularly-reflected light tends to vary "from (1) gradually decreasing to (2) reaching the extreme value to (3) gradually increasing to (4) becoming substantially constant", as shown in the upper graph in FIG. 4. This tendency itself is invariable, regardless of changes in various conditions (such as the attachment position of the optical sensor 23a, the attachment position of the light emission unit 22, temporal or spatial fluctuations in the amount of light emitted from the light emission unit 22, the pattern to be formed, the type and the thickness of the base material X, the amount of discharged particle dispersed liquid Y, the type and the amount of the particle dispersed liquid Y, and environmental conditions). The amount of diffusely-reflected light tends to change in the opposite manner of the amount of specularly-reflected light.

Taking advantage of the above described tendency, the calcination apparatus 1 can accurately determine completion of calcination. That is, the calcination apparatus 1 determines that calcination is completed when the amount of reflected light reaches the stage of "(4) becoming substantially constant", and recognizes completion of the calcination. More specifically, after the detected value of the amount of reflected light has already reached the extreme value, and when the temporal variation of this value falls within a predetermined range, the calcination apparatus 1 determines that securing of the particles by calcination is completed. This predetermined range is set in such a range that the temporal variation can be considered having become almost zero, with allowable errors and the like being taken into consideration. In this embodiment, the predetermined range is set within ±2% of the amount of reflected light at the time, for example.

When the calcination is determined to be completed, the output unit 23d outputs a signal for suspending the supply of calcination energy, to the calcination condition adjustment unit 24. With this signal, the calcination condition adjustment unit 24 suspends the supply of calcination energy from the calcination unit 21a. As a result, the calcination apparatus 1 can supply exactly the right amount of calcination energy for calcination, and realize appropriate calcination.

Various specific methods can be used in determining the time "when the detected value of the amount of reflected light has already reached the extreme value, and the temporal variation of this value falls within a predetermined range" to be the time of completion of calcination. In this embodiment, the following method is employed as an example: the reflected light amount monitoring unit 23 is designed to detect the amount of specularly-reflected light, the variation of the output of the operating unit 23c from "negative to positive to zero (within ±2% of the amount of reflected light)" is observed, and completion of calcination is detected when the output of the operating unit 23c becomes "zero". If the output of the operating unit 23c does not become "zero" even after a predetermined period of time has passed, the output unit 23d may output a signal for increasing the calcination energy to the calcination condition adjustment unit 24.

As another example, the following method may be employed: the reflected light amount monitoring unit 23 is designed to detect the amount of diffusely-reflected light, the variation of the output of the operating unit 23c from "positive to negative to zero (within ±2% of the amount of reflected light)" is observed, and completion of calcination is detected when the output of the operating unit 23c becomes "zero". If the output of the operating unit 23c does not become "zero" even after a predetermined period of time has passed in this example, the output unit 23d may also output a signal for increasing the calcination energy to the calcination condition adjustment unit 24.

[Modifications of the Calcination Unit]

The form of the above described calcination unit (the calcination unit 21a in the example case shown in FIG. 2) can be modified in various manners, without departing from the scope thereof. Referring now to FIGS. 5 through 8, several modifications of the calcination unit are described.

Figure 5:
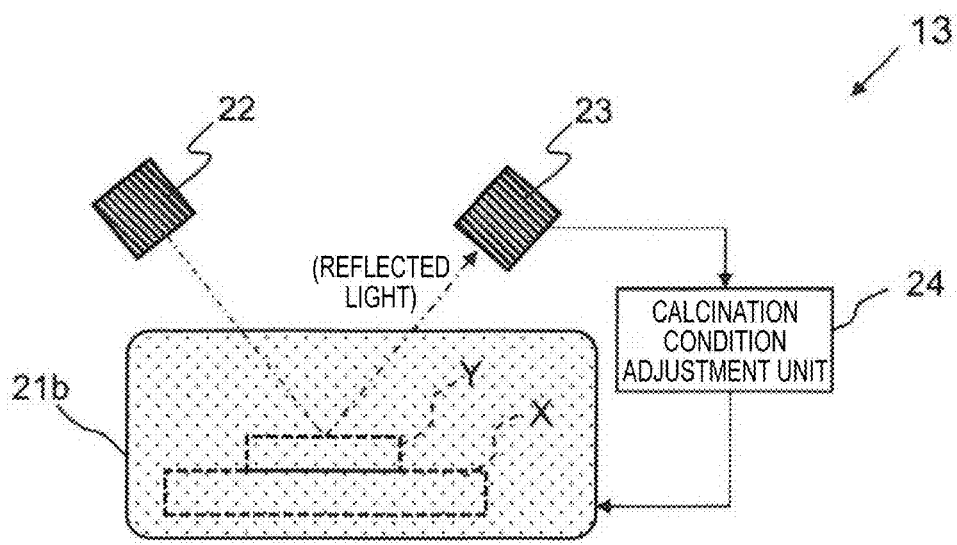
FIG. 5 is a diagram for explaining a modification of a calcination unit.

The calcination unit 21b shown in FIG. 5 is in the form of a furnace that accommodates the base material X having the particle dispersed liquid Y applied thereto, supplies calcination energy mainly by convection to calcine the particle dispersed liquid Y. Thermal calcination involving a hot plate or a furnace can be readily performed, compared with other calcination techniques.

Figure 6:
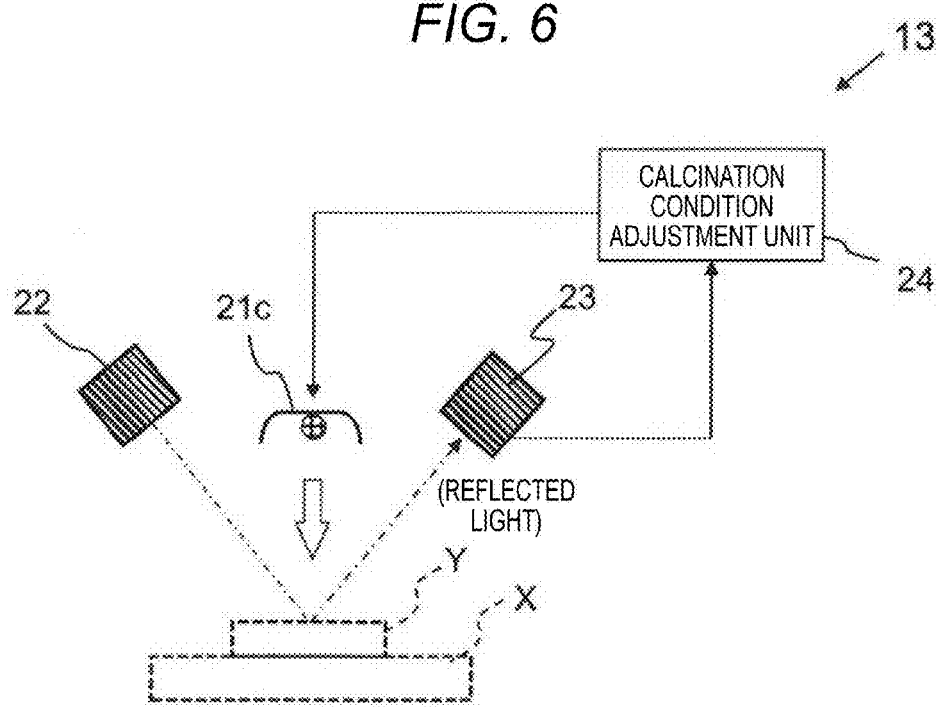
FIG. 6 is a diagram for explaining another modification of the calcination unit.
Figure 7:
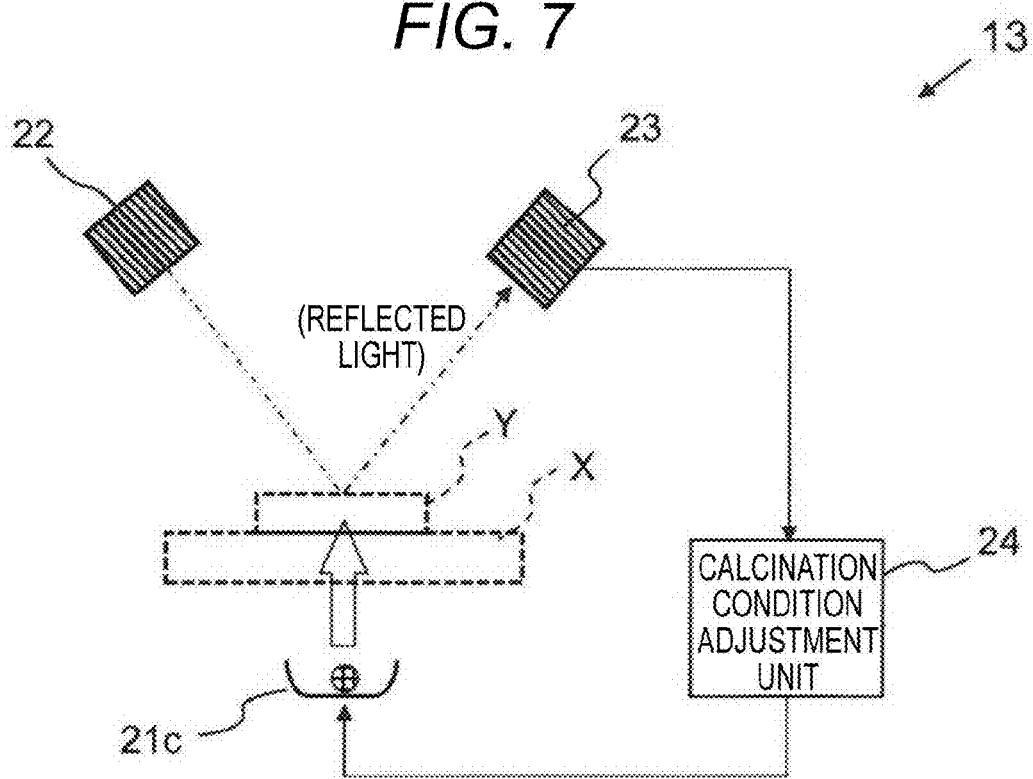
FIG. 7 is a diagram for explaining yet another modification of the calcination unit.

Each of the calcination units 21c shown in FIGS. 6 and 7 is in the form of a light source (such as a xenon lamp) that emits light toward the particle dispersed liquid Y, and supplies calcination energy mainly by radiation to calcine the particle dispersed liquid Y. The calcination unit 21c shown in FIG. 6 is designed to emit light to the front side (the side to which the particle dispersed liquid Y is applied) of the base material X, and the calcination unit 21c shown in FIG. 7 is designed to emit light to the back side of the base material X. Optical calcination involving a light source can be performed in a shorter time, compared with other calcination techniques.

Figure 8:
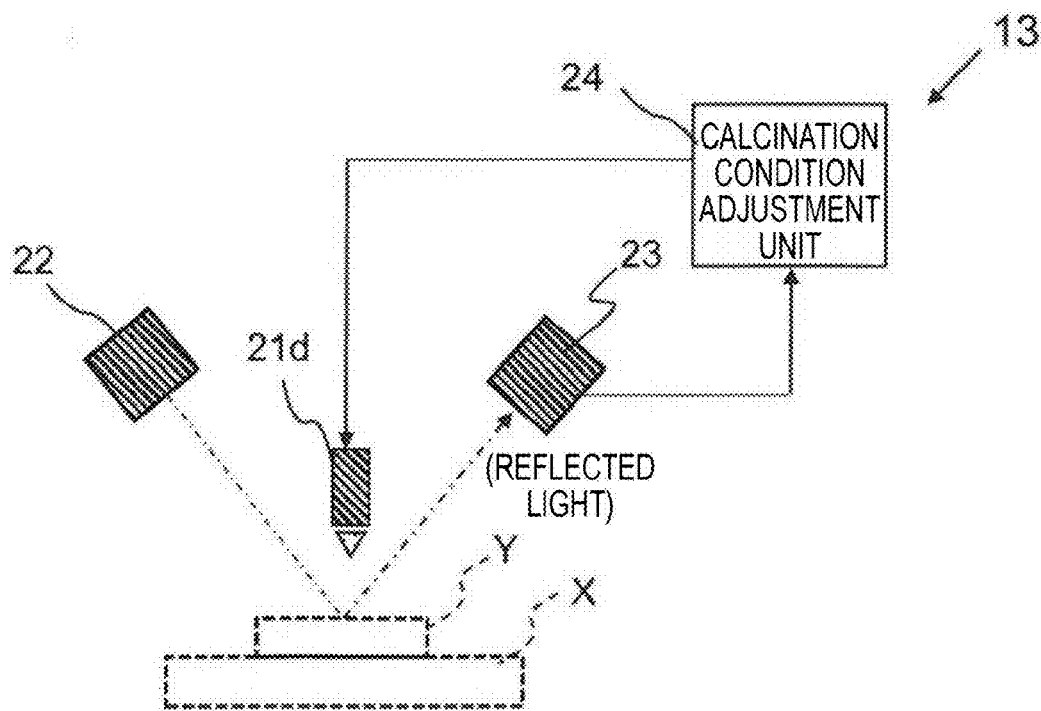
FIG. 8 is a diagram for explaining still another modification of the calcination unit.

The calcination unit 21d shown in FIG. 8 is in a form that converts chemical energy into calcination energy, and applies a dispersant remover to the particle dispersed liquid Y. As the dispersant remover is applied, the dispersant that disperses the particles in the solvent is removed, and as a result, the particles are sintered. Chemical calcination involving a dispersant remover can be performed without any device for supplying direct energy such as heat or light. When calcination is performed with the calcination unit 21d, heat may be applied in an auxiliary manner. Alternatively, room temperature may be used as calcination energy.

[Coating with an Antireflection Film]

In a case where the base material X enters the spot (optical spot) of light emitted to the particle dispersed liquid Y, the state of the surface of the base material X affects the amount of reflected light and the temporal variation of the amount. In a case where thermal paper as the base material X is used in thermal calcination, for example, the surface of the thermal paper changes in color at the start of the calcination, and the amount of reflected light also varies. In such a case, the surface of the base material X to which the particle dispersed liquid Y is to be applied is preferably coated with an antireflection film, prior to application of the particle dispersed liquid Y. The entire surface of the base material X may be coated with the antireflection film, or the portion on which a pattern of the particle dispersed liquid Y is to be formed may be coated with the antireflection film.

As the coating with the antireflection film is performed, the state of the surface of the base material X can be prevented as much as possible from affecting the amount of reflected light and the temporal variation of the amount. The coating with the antireflection film may be performed by either a wet process such as roll coating, gravure coating, spin coating, or spraying, or a dry process such as vacuum deposition, sputtering, or CVD. In a case where the portion on which a pattern of the particle dispersed liquid Y is to be formed is coated, a mask that conforms to shape of the pattern may be formed, and the portion is then coated with the antireflection film. In a case where the antireflection film is formed on a transparent PET film, $MgF_2$ is preferably used as the material of the antireflection film.

In a case where the base material X is coated with the antireflection film, the method used in calcining the particle dispersed liquid Y on the base material X may be a method that includes: (1) a first step of forming the antireflection film on the surface of the base material X to which the particle dispersed liquid Y is to be applied; (2) a second step of applying the particle dispersed liquid Y to the base material X after the first step is carried out; and (3) a third step of causing the calcination processing unit 13 to perform a calcination process after the second step is carried out.

[Installation of Plurality of Pairs of Light Emission Units and Reflected Light Amount Monitoring Units]

In a case where the thickness of the base material X or the amount of the particle dispersed liquid Y to be applied varies, if there is only one pair of the light emission unit 22 and the reflected light amount monitoring unit 23, completion of calcination might be wrongly determined, though there is a site where calcination is insufficient.

Figure 9:
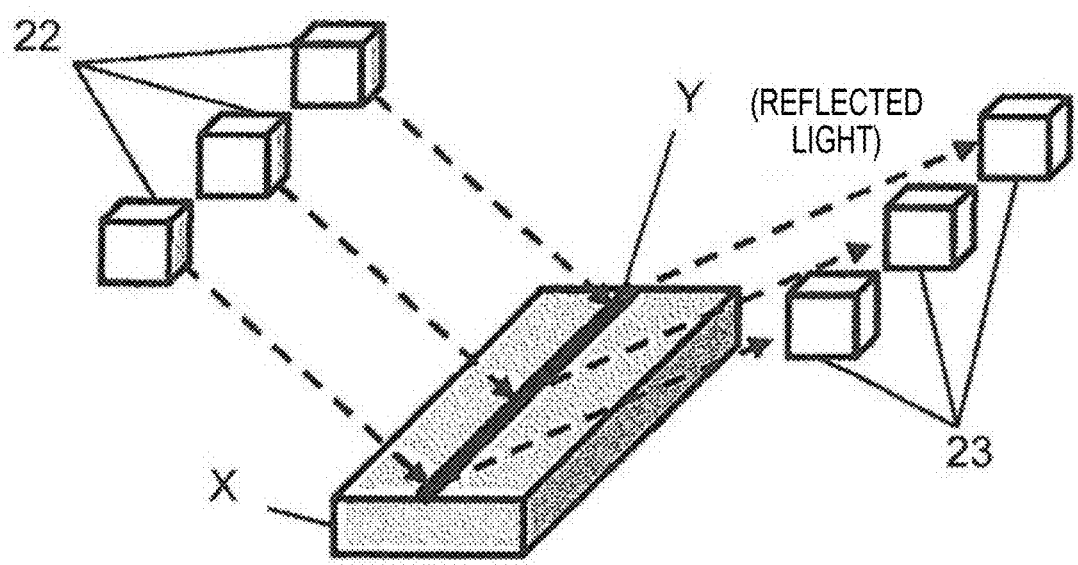
FIG. 9 is a diagram for explaining installation of a plurality pairs of light emission units and reflected light amount monitoring units.

In view of this, as shown in FIG. 9, a plurality of pairs of light emission units 22 and reflected light amount monitoring units 23 may be provided so as to detect amounts of reflected light at different locations on the surface of the particle dispersed liquid Y, the light emission unit corresponding reflected light amount monitoring unit with each other. As shown in FIG. 9, these pairs are located on the side to which the particle dispersed liquid Y is applied, with the surface of the base material X being the reference surface.

In a case where the pairs of the light emission units 22 and the reflected light amount monitoring units 23 are provided at 100 locations so as to monitor a sample of 300 mm in width, for example, the calcination state can be monitored at 3-mm intervals. With this, even if there is a site where the calcination energy becomes insufficient due to variations or the like in the calcination conditions, the calcination state can be monitored as closely as possible.

[Comparative Evaluations of Respective Examples]

Next, the results of evaluations of calcination states (surface states of wiring patterns and resistance values) in respective Examples of the present invention are described, with reference to Tables 1 through 4. In each of the tables, "excellent" indicates a calcination state (a calcination state that is preferable over a wide range) in which the conductivity at any site in the conductive pattern is constant within a cataloged value range. Meanwhile, "good" indicates a calcination state (a preferable calcination state) in which the conductivity is within the cataloged value range.

Further, "poor" indicates a calcination state with a calcination defect due to an excess or shortage of calcination energy. More specifically, "poor (excess)" indicates a state in which conductivity cannot be measured due to an excessive supply of calcination energy, or a calcination state in which cracks or breaks can be visually confirmed. On the other hand, "poor (insufficient)" indicates a state in which conductivity cannot be measured due to a shortage of calcination energy supply, or a calcination state with no metallic luster.

First, the results of a comparative evaluation conducted on Example 1 and Comparative Example 1 are described. The common conditions in Example 1 and Comparative Example 1 are as follows.

Particle dispersed liquid: Ag nanoink (NPS-JL, manufactured by Harima Chemicals, Inc.)
Application pattern: straight line of 100 μm in width
Light source: halogen lamp (QR, manufactured by USHIO INC.)
Optical sensor: Si photodiode (S12158-01CT, manufactured by Hamamatsu Photonics K.K.)
Base material: PET sheet (manufactured by LMS Co., Ltd.)
Calcination unit: hot plate (RSH-10N, manufactured by ASONE Corporation) However, while completion of calcination was determined based on a difference (a temporal variation) between the current amount of reflected light and the previous amount of reflected light in Example 1, completion of calcination was determined based on a comparison with the absolute value of an already measured amount of light reflected from a base material of approximately 100 μm in thickness in Comparative Example 1. Except for this aspect, the conditions in Example 1 and Comparative Example 1 are basically the same. In each of Example 1 and Comparative Example 1, the evaluation was conducted in the three cases where the base material thickness was 10 μm, 100 μm, and 1000 μm, which served as variations in the calcination conditions. The results of the evaluation conducted under the conditions are shown in Table 1.

TABLE 1

|  | Example 1 | | | Comparative Example 1 | | |
| --- | --- | --- | --- | --- | --- | --- |
|  | 1-1 | 1-2 | 1-3 | 1-1 | 1-2 | 1-3 |
| Determination method | Based on difference (temporal variation) | | | Based on comparison with absolute value | | |
| Variation in base material thickness (μm) | 10 | 100 | 1000 | 10 | 100 | 1000 |
| Calcination state | good | good | good | poor (excessive) | good | poor (insufficient) |

In Comparative Example 1, when a 10-μm thick base material having a small heat capacity is used, the base material is damaged due to excessive calcination, and the wiring pattern is broken. When a 1000-μm thick base material having a large heat capacity is used, a shortage of calcination energy occurs, and the solvent, the dispersant, or non-bonded particles remain. Therefore, an appropriate wiring pattern is not formed. In Example 1, on the other hand, the amount of calcination energy supply appropriately changes with the various thicknesses of base materials.

Accordingly, preferable calcination is realized, regardless of the base material thicknesses.

Next, the results of a comparative evaluation conducted on Example 2 and Comparative Example 2 are described. The common conditions in Example 2 and Comparative Example 2 are as follows.

Particle dispersed liquid: Ag nanoink (NPS-JL, manufactured by Harima Chemicals, Inc.)
Application pattern: straight line of 100 μm in width
Light source: halogen lamp (QR, manufactured by USHIO INC.)
Optical sensor: Si photodiode (S12158-01CT, manufactured by Hamamatsu Photonics K.K.)
Base material: PET sheet (manufactured by LMS Co., Ltd.)
Calcination unit: hot plate (RSH-10N, manufactured by ASONE Corporation)

However, while completion of calcination was determined when the temporal variation in the amount of reflected light became almost zero after reaching the extreme value in Example 2, completion of calcination was determined when the temporal variation in the amount of reflected light became almost zero regardless of whether the amount of reflected light had reached the extreme value in Comparative Example 2. Except for this aspect, the conditions in Example 2 and Comparative Example 2 are basically the same. The results of the evaluation conducted under the conditions are shown in Table 2.

TABLE 2

|  | Example 2 | Comparative Example 2 |
|---|---|---|
| Particle dispersed liquid | Conductive ink | Conductive ink |
| Determination method | Based on difference (temporal variation) | |
| Determination criterion | Temporal variation is almost zero after reaching extreme value | Temporal variation is almost zero, regardless of extreme value |
| Calcination state | good | poor (insufficient) |

In Comparative Example 2, whether the amount of reflected light has reached the extreme value is not taken into consideration. Therefore, when the amount of reflected light hardly changes at the start of exposure of conductive particles through the surface and bonding between the conductive particles, the temporal variation in the amount of reflected light becomes almost zero, and, at this point, completion of calcination is wrongly determined. As a result, a shortage of calcination energy occurs, and an appropriate wiring pattern is not formed. In Example 2, on the other hand, even when the temporal variation becomes almost zero before the amount of reflected light reaches the extreme value, completion of calcination is not determined. Accordingly, calcination energy is appropriately supplied, and preferable calcination is realized.

Next, the results of an evaluation conducted on Example 3 and Example 4 are described. The common conditions in Example 3 and Example 4 are as follows.

Particle dispersed liquid: Ag nanoink (NPS-JL, manufactured by Harima Chemicals, Inc.)
Application pattern: straight line of 60 μm in width
Light source: halogen lamp (QR, manufactured by USHIO INC.)
Optical spot size: 100 μm
Optical sensor: Si photodiode (S12158-01CT, manufactured by Hamamatsu Photonics K.K.)
Base material: thermal paper (manufactured by Mitsubishi Paper Mills Limited.)
Calcination unit: hot plate (RSH-10N, manufactured by ASONE Corporation)

However, while an antireflection coating ($MGF_2$) is provided beforehand on the surface of the base material in Example 3, any antireflection coating is not provided in Example 4. Except for this aspect, the conditions in Example 3 and Example 4 are basically the same. The results of the evaluation conducted under the conditions are shown in Table 3.

TABLE 3

|  | Example 3 | Example 4 |
|---|---|---|
| Antireflection coating | Provided | Not Provided |
| Calcination state | excellent | good |

In Example 3, even if a portion of the base material is included in the optical spot, reflection from the portion of the base material is substantially prevented by the antireflection coating, and the amount of light reflected from the portion of the base material hardly affects the result of detection performed by the optical sensor. Accordingly, preferable calcination was realized at any location in the conductive pattern. In Example 4, on the other hand, a portion of the base material is included in the optical spot, and therefore, the amount of light reflected from the portion of the base material affects the result of detection performed by the optical sensor. As a result, a generally preferable calcination state is realized, but the excellent calcination state realized in Example 3 is not achieved.

Next, the results of an evaluation conducted on Examples 5 through 7 are described. The common conditions in Examples 5 through 7 are as follows.

Particle dispersed liquid: Ag nanoink (NPS-JL, manufactured by Harima Chemicals, Inc.)
Application pattern: straight line of 100 μm in width
Light source: halogen lamp (QR, manufactured by USHIO INC.)
Optical sensor: Si photodiode (S12158-01CT, manufactured by Hamamatsu Photonics K.K.)
Base material: PET sheet (300 mm in width, manufactured by LMS Co., Ltd.)
Calcination unit: hot plate (RSH-10N, manufactured by ASONE Corporation)

However, while only one pair of a light emission unit and a reflected light amount monitoring unit is provided in Example 5, 10 pairs are provided in Example 6, and 100 pairs are provided in Example 7. Except for this aspect, the conditions in Examples 5 through 7 are basically the same. The results of the evaluation conducted under the conditions are shown in Table 4.

TABLE 4

|  | Example 5 | Example 6 | Example 7 |
|---|---|---|---|
| Number of pairs of light emission units and reflected light amount monitoring units | 1 | 10 | 100 |

TABLE 4-continued

|  | Example 5 | Example 6 | Example 7 |
|---|---|---|---|
| Calcination state (variation in calcination state with location) | good | good | excellent |

Even in a case where there are variations in the thickness of the base material, the amount of applied particle dispersed liquid, and the like, if a large number of pairs of light emission units and reflected light amount monitoring units are installed, completion of calcination can be appropriately determined when preferable overall calcination is performed. For this reason, the most preferable calcination state is realized in Example 7 as shown in Table 4.

[Other Aspects]

As described above, the calcination apparatus 1 is an apparatus that performs a particle securing process (a calcination process in this embodiment) on the particle dispersed liquid Y applied onto the base material X, to remove the solvent and secure the particles onto the base material X. The calcination apparatus 1 includes: the light emission unit 22 that emits light to the surface of the particle dispersed liquid Y; the reflected light amount monitoring unit 23 that detects the amount of the light reflected, and monitors a temporal variation of the detected value; and the calcination condition adjustment unit 24 that adjusts the conditions for the particle securing process.

Furthermore, when the value has already reached the extreme value, and the temporal variation of this value falls within a predetermined range (a range within ±2% of the detected amount of the reflected light), the calcination apparatus 1 determines that securing of the particles is completed. Accordingly, with the calcination apparatus 1, a calcination process can be performed in a more appropriate manner, regardless of variations in respective conditions.

Although a calcination process has been described as the particle securing process in this embodiment, specific examples of the particle securing process are not limited to the above. For example, the particle securing process may be a process to be performed on a liquid developer (an example of the particle dispersed liquid, having toner particles dispersed therein) applied to a base material such as paper or OHP, so as to remove the solvent and secure the toner particles onto the base material.

The present invention can be used in various fields to which printed electronics (PE) is applied, for example.

According to an embodiment of the present invention, with the processing apparatus, a process such as calcination can be performed in a more appropriate manner, regardless of variations in respective conditions. By the particle securing method according to another aspect of the present invention, a decrease in the accuracy of the determination due to influence of the amount of light reflected from a portion of the base material can be prevented as much as possible.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A processing apparatus comprising:
   a light emission unit configured to emit light to a surface of a particle dispersed liquid applied to a base material, the particle dispersed liquid having particles dispersed in a solvent;
   a reflected light amount monitoring unit configured to detect an amount of the light reflected, and monitor a temporal variation of the detected value; and
   a condition adjustment unit configured to adjust a condition for a particle securing process, the particle securing process being performed to remove the solvent and secure the particles onto the base material,
   wherein, when the temporal variation falls within a predetermined range after the value has reached an extreme value, securing of the particles is determined to have been completed.

2. The processing apparatus according to claim 1, wherein the particle securing process is a process of calcining the particle dispersed liquid through a supply of calcination energy, and,
   when the securing of the particles by calcination is determined to have been completed, the supply of calcination energy is suspended.

3. The processing apparatus according to claim 1, wherein the reflected light amount monitoring unit calculates the temporal variation by recognizing the value in each predetermined time interval, and calculating a difference between the value and the value detected last time.

4. The processing apparatus according to claim 3, wherein the predetermined range is set as a range within ±2% of the detected amount of the light reflected.

5. The processing apparatus according to claim 1, wherein a plurality pairs of light emission units and reflected light amount monitoring units are installed to detect amounts of reflected light at different locations on the surface of the particle dispersed liquid, the light emission unit and the reflected light amount monitoring unit being corresponded to each other.

6. A particle securing method using the processing apparatus of claim 1 to secure the particles onto the base material, the particle securing method comprising:
   a first step of coating a surface of the base material with an antireflection film, the particle dispersed liquid being applied to the surface of the base material;
   a second step of applying the particle dispersed liquid to the base material after the first step is carried out; and
   a third step of causing the processing apparatus to perform the particle securing process after the second step is carried out.

7. The particle securing method according to claim 6, wherein
   the particle securing process is a process of calcining the particle dispersed liquid through a supply of calcination energy, and,
   when the securing of the particles by calcination is determined to have been completed, the supply of calcination energy is suspended.

8. The particle securing method according to claim 6, wherein the reflected light amount monitoring unit calculates the temporal variation by recognizing the value in each predetermined time interval, and calculating a difference between the value and the value detected last time.

9. The particle securing method according to claim 8, wherein the predetermined range is set as a range within ±2% of the detected amount of the light reflected.

10. The particle securing method according to claim 6, wherein pairs of light emission units and reflected light amount monitoring units are installed to detect amounts of reflected light at different locations on the surface of the particle dispersed liquid, the light emission unit and the reflected light amount monitoring unit being corresponded to each other.

11. The processing apparatus according to claim 1, wherein
- the reflected light amount monitoring unit is configured to detect the amount of the light reflected as a detected value, and
- the extreme value is either a highest detected value or a lowest detected value, the predetermined range being lower than the extreme value when the extreme value is the highest detected value and the predetermined range being higher than the extreme value when the extreme value is the lowest detected value.

\* \* \* \* \*